United States Patent
Khamar et al.

(10) Patent No.: US 10,335,472 B2
(45) Date of Patent: Jul. 2, 2019

(54) THERAPEUTIC CANCER VACCINE

(71) Applicant: Cadila Pharmaceuticals Ltd., Ahmedabad (IN)

(72) Inventors: Bakulesh Mafatlal Khamar, Ahmedabad (IN); Nirav Manojkumar Desai, Ahmedabad (IN); Chandreshwar Prasad Shukla, Ahmedabad (IN); Avani Devenbhai Darji, Ahmedabad (IN); Indravadan Ambalal Modi, Ahmedabad (IN)

(73) Assignee: Cadila Pharmaceuticals Ltd. (IN)

( * ) Notice: Subject to any disclaimer, the term of this patent is extended or adjusted under 35 U.S.C. 154(b) by 0 days.

(21) Appl. No.: 15/410,842

(22) Filed: Jan. 20, 2017

(65) Prior Publication Data

US 2017/0157231 A1  Jun. 8, 2017

Related U.S. Application Data

(62) Division of application No. 14/001,795, filed as application No. PCT/IB2012/050876 on Feb. 27, 2012, now abandoned.

(30) Foreign Application Priority Data

Feb. 28, 2011  (IN) ............................ 555/MUM/2011

(51) Int. Cl.
| | |
|---|---|
| *A61K 35/00* | (2006.01) |
| *A61K 39/00* | (2006.01) |
| *A61K 39/04* | (2006.01) |
| *A61K 9/00* | (2006.01) |

(52) U.S. Cl.
CPC ........ *A61K 39/0011* (2013.01); *A61K 9/0021* (2013.01); *A61K 39/04* (2013.01); *A61K 2039/5152* (2013.01); *A61K 2039/54* (2013.01); *A61K 2039/55594* (2013.01); *A61K 2039/572* (2013.01); *A61K 2039/575* (2013.01)

(58) Field of Classification Search
CPC .................. A61K 38/00; A61K 2039/5152
See application file for complete search history.

(56) References Cited

U.S. PATENT DOCUMENTS

| | | | |
|---|---|---|---|
| 7,977,095 B2 * | 7/2011 | Bonyhadi | ............ C12N 5/0636 435/372.3 |
| 8,277,778 B2 | 10/2012 | Khamar et al. | |
| 2010/0104536 A1 | 4/2010 | Modi et al. | |
| 2012/0308605 A1 | 12/2012 | Khamar et al. | |
| 2013/0011430 A1 | 1/2013 | Singh et al. | |

FOREIGN PATENT DOCUMENTS

| | | |
|---|---|---|
| WO | 2003049751 | 6/2003 |
| WO | 2006114680 | 11/2006 |
| WO | 2008114119 | 9/2008 |

OTHER PUBLICATIONS

Lollini et al. (Curr. Cancer Drug Targets. May 2005; 5 (3): 221-228).*
Lollini et al. (Trends Immunol. Feb. 2003; 24 (2): 62-66).*
Slingluff et al. (Cancer Immunol. Immunother. Mar. 2000; 48 (12): 661-672).*
Arceci (Journal of Molecular Medicine. 1998; 76: 80-93).*
Khong et al. (Nat. Immunol. Nov. 2002; 3 (11): 999-1005; pp. 1-17).*
Neeley et al. (Prostate. May 15, 2008; 68 (7):715-27).*
Restifo et al. (J. Natl. Cancer Inst. Jan. 17, 1996; 88 (2): 100-8; pp. 1-19).*
Cuenda et al. (Biochim. Biophys. Acta. Aug. 2007; 1773 (8): 1358-75).*
Bodey et al. (Anticancer Research. 2000; 20: 2665-2676).*
Gura (Science. 1997; 278: 1041-1042).*
Matsushita et al. (Nature. Feb. 8, 2012; 482 (7385): 400-4).*
Genßler et al. (Oncoimmunology. Dec. 21, 2015; 5 (4): e1119354; pp. 1-12).*
Chistiakov et al. (Eur. J. Pharmacol. Sep. 5, 2017; 810: 70-82).*
Sampson et al. (J. Clin. Oncol. Nov. 1, 2010; 28 (31): 4722-9).*
Furnari et al. (Nat. Rev. Cancer. May 2015; 15 (5): 302-10).*
Del Vecchio et al. (Expert Rev. Vaccines. Feb. 2012; 11 (2): 133-44).*
Tang et al. (Clin. Cancer Res. Jul. 15, 2005; 11 (14): 5292-9).*
Wang et al. (Exp. Opin. Biol. Ther. 2001; 1 (2): 277-290).*
Shimato et al. (BMC Cancer. Nov. 27, 2012; 12: 561; pp. 1-9).*
Kuball et al. (Cancer Immunol. Immunother. Feb. 2011; 60 (2): 161-71).*
Welsh et al. (Curr. Opin. Immunol. Jun. 2004; 16 (3): 271-6).*
Pomerance et al. "High-level expression, activation, and subcellular localization of p38-MAP kinase in thyroid neoplasma" J. Pathol. Mar. 2006; 209: 298-306.
Douziech et al. "Growth Effects of Regulatory Peptides and Intracellular Signaling Routes in Human Pancreatic Cancer Cell Lines" Endocrine Oct. 1998; 9 (2): 171-83.
Yang at al. "p38γ overexpression in gliomas and its role in proliferation and apoptosis" Sci. Rep. Jun. 2013; 3: 2089; 1-5.
Yarkoni et al. "Eradication by Active Specific Immunotherapy of Established Tumor Transplants and Microscopic Lymph Node Metastases" Cancer Res. Jul. 1982; 42 (7): 2544-2546.
Yunis at al. (Int. J. Cancer. Jan. 1977; 19 (1): 128-35).
Lutz et al. "A Lethally Irradiated Allogeneic Granulocyte-Macrophage Colony Stimulating Factor-Secreting Turnor Vaccine for Pancreatic Adenocarcinoma; A Phase II Trial of Safety, Efficacy, and Immune Activation" Ann. Surg, Feb. 2011; 253 (2): 328-335 pp. 1-18.

(Continued)

*Primary Examiner* — Stephen L Rawlings

(74) *Attorney, Agent, or Firm* — Burns & Levinson, LLP; Shahid Hasan

(57) ABSTRACT

The present invention relates to vaccine(s) comprising cancer cells expressing antigen(s), excipients, optionally adjuvant wherein the said antigen(s) is expressed on contacting the said cancer cell with p38 inducer, for use in treatment of Cancer. The vaccine composition induces specific immune response against homologous and heterologous cancer cells of the tissue/organ. The invention also provides method of preparing the same.

7 Claims, 5 Drawing Sheets

(56) References Cited

OTHER PUBLICATIONS

Jaffee et al. "Clinical Protocol: A Phase I Clinical Trail of Lethally Irradiated Allogeneic Pancreatic Tumor Cells Transfected with the GM-CSF Gene for the Treatment of Pancreatic Adenocarcinoma" Hum. Gene Ther. Sep. 1998; 9:1951-1971).
Von Euw et al. (J. Transl. Med. Jan. 25, 2006; 6: 6; pp. 1-14).
Hrouda et al "Allogeneic whole-tumour cell vaccination on the rat model of prostate cancer" BJU Int. Jul. 2000; 86 (6): 742-748.
Sur et al. (J. Indian Med. Assoc. Feb. 2003; 101 (2):118, 120).
Dennis (nature. Aug. 7, 2006; 442: 739-741).
Gure (Science. 1997; 278: 1041-1042).
Schuh (Toxixologic Pathology, 2004: 32 (Suppl. 1): 53-66).
Peterson et al. (Eur. J. Cancer, 2004; 40: 837-844).
Lens "The role of vaccine therapy in the treatment of melanoma" Expert Opin, Biol Ther. Mar. 2008; 8 (3): 315-323.
Xia et al. (Cell. Res. Mar. 2006; 16 (3): 241-259).
Schietinger et al. (Sermin. Immunol. Oct. 2008; 20 (5). 276-852).
Prehn (Cancer Cel Int. Aug. 1, 2005; 5 (1): 25; pp. 1-5).
Morris et al. (Surg. Oncol. Clin. N. Am. Oct. 2007; 16 (4): 819-831).
Finke et al. (Immunol. Today. Apr. 1999; 20 (4): 158-160).
Jiang X P et al. (Radiopharmaceuticals, Liberty, Jan. 1, 2000; 15 (5): 495-505).
Sur Prabir Kumar at al. (J. Indian Med. Ass. Jan. 1, 2003; 101 (2): 118-120).
Tortorella et al. (Mechanics of Ageing and Dev. Aug. 1, 2004: 125 (8): 539-546).
Moingeon et al. (Vaccine, Elsevier Dec. 8, 2001; 19 (11-12).
International Search Reoprt issued by the PCT in corresponding PCT application PCT/IB2012/050876, dated Jul. 7, 2012.

* cited by examiner

Loading Pattern Gel-1
Lane 1: Blank
Lane 2: MiaPaCa-2 cell lysate
Lane 3: SW-1990 cell lysate
Lane 4: AsPC-1 cell lysate
Lane 5: HEK 293 cell lysate Loading Pattern Gel-2
Lane 1 - PC-3 cell lysate (Prostrate cancer)
Lane 2 - MCF-7 cell lysate (Breast cancer)
Lane 3 - A549 cell lysate (Lung cancer)
Lane 4 - PA-1 cell lysate (Ovarian cancer)
Lane 5 - A375 cell lysate (Melanoma)
Lane 6 - Unstained protein marker

THERAPEUTIC CANCER VACCINE

CROSS REFERENCE TO RELATED APPLICATION

This application is a divisional application and claims the benefit of co-pending U.S. application Ser. No. 14/001,795 filed Aug. 27, 2013, which is a § 371 U.S. National Stage of PCT Application No. PCT/M2012/050876, filed Feb. 27, 2012, which was published in English under PCT Article 21(2) as WO2012117323 on Sep. 7, 2012, which in turn claims the benefit of and priority to the Indian Application No. 555/MUM/2011, filed on Feb. 28, 2011, each of which is incorporated by reference herein in its entirety.

FIELD OF INVENTION

The present invention relates to therapeutic vaccines, for use in treatment of malignant tumors, having immunogenicity against heterogeneous cancer antigen/s specific to tissue/organ. The invention also provides method of preparing the same.

BACKGROUND

Malignant tumors are known to have many different types of cells in it. These cells have genes and proteins that are very different from one another. And they grow at different rates. This is known as heterogeneity. The heterogeneity is also responsible for combining chemotherapy with radiotherapy and/or various kind of chemotherapy in combination for effective treatment of malignant tumors.

There is a lack of well defined antigens for organ/tissue specific cancer. To overcome this problem cancer cells are used as an antigen. The use of cancer cells provides benefit of repertoires of the antigens present on cancer cells.

The cancer cells can be sourced from the same patients (autologous) or from a different patient (allogeneic).

Use of autologous cancer cell in vaccines is personalized therapy and is associated with practical difficulties. The autologous cells may not be available in all patients. When available it may not be of the desired quality and/or quantity. The approach is also time consuming. The approach is also associated with regulatory hurdles.

Use of allogeneic cancer cells is attractive as an antigen in therapeutic vaccine. However it suffers from lack of common antigen/s as cancer cells from a tissue/organ are heterogeneous in nature. The allogeneic cancer cells fail to elicit immune response against heterogeneous cancer cells specific to a tissue/organ. e.g. Allogeneic cell lines of pancreatic cancer Mia-paca-2 and Panc-1 produce immune response against themselves. However Mia-pica-2 cell line fails to elicit immune response against Panc-1 and Panc-1 fails to elicit immune response against Mia-paca-2

This can be overcome by use of multiple heterogeneous allogeneic cancer cells in a vaccine or identifying antigen present in a cancer tissue and using specific vaccine against it.

The heterogeneity of tumor makes it difficult to have a therapeutic vaccine with a single antigen to provide immune response against all the cells/majority of cells contained in the tumor. For this reason one need to combine allogeneic cells/antigens for therapeutic vaccine to make it effective against the tumor as a whole.

To overcome the problem of heterogeneity of the cancer/tumors, it is demonstrated to use more than one cell as antigen. Emens et al demonstrated use of more then one allogeneic cell line to cover the antigen repertoire of the heterogenic tumor/cancer. (Emens L A et al; J Clin Oncol. 2009 Dec. 10; 27(35):5911-8). While Laheru D et al demonstrated use of GM CSF to improve immunogenicity of the allogeneic cancer cells vaccine for treatment of cancer. Clin Cancer Res. 2008 Mar. 1; 14(5):1455-63).

Formalin-fixed tumor cells effectively induce anti-tumor immunity both in prophylactic and therapeutic conditions was explained by Chikage Obata, in Journal of dermatological science, Volume 34, issue 2, Pages 209-219 (May 2004) while a Clinical trial of autologous formalin-fixed tumor vaccine for glioblastoma multiform patients studied by Ishikawa E, in Cancer Sci. 2007 August; 98(8):1226-33, Epub 2007 May 22. In both the studies the efficacy is against the homologous cancer cells/tumors but none have demonstrated the killing of hetrogenous cancer cells specific to tissue/organ are killed by the vaccine.

Thus there is a need to have therapeutic vaccine using allogeneic cells as antigen for use in treatment of cancers which elicits immune response against heterogeneous cancer antigen/s specific to tissue/organ. E.g. therapeutic vaccine for pancreatic cancer using Mia-paca-2 cell line elicits immune response against Panc-1 and other pancreatic cancer cells.

Heterogeneous cancer cells specific to tissue/organ are those cancer cells which are present/originate from the same tissue/organ but fail to elicit and/or react to immune response generated by cancer cells which are present/originate from the same tissue/organ.

The methods for harvesting cancer cells and preserving them or propagating them are well known. The methods can be used for autologous as well as allogeneic cells, Some of the allogeneic cancer cell lines which are available for various type of tumors are listed below. The cell lines can be procured from various repositories like American Type Culture Collection, USA; Cell bank Australia, Australia; Coriell Cell Repositories, New Jersey USA; European Collection of Cell Cultures (ECACC), UK; German Collection of Microorganisms and Cell Cultures, Germany; Japanese Collection of Research Bioresources (JCRB), Japan; German Collection of Microorganisms and Cell Cultures, Germany; Korean Cell bank, Korea; RIKEN Bioresource Centre, Japan; Human Genetics Resource Center, USA; National Centre for Cell Science, India; MMRRC: Mutant Mouse Regional Resource Centers, USA; National Human Neural Stem Cell Resource, USA; UK Stem Cell Bank, UK and NCCS in India.

Also these or new cell lines or specific cancer cells can be isolated as described by Eton O, et al. Active immunotherapy with B irradiated Autologous whole Melanoma cells plus DETOX in patients with metastatic melanoma. In clinical cancer research, March 1998, Vol. 4, 619-627. Fresh tumor was collected at the time of surgery from frozen section laboratory and fragmented by slicing. to maximize the yield of viable tumor cells for vaccine preparation, the bulk of tumor was dissociated using collagenase type 1 (2 mg/ml) and type IV DNase (0.4 mg/ml) Sigma chemical Co., St Loius, Mo.; ref 25. These enzymes can alter the immunogenicity of the resulting cell preparation. The dissociated cells were washed in HBSS and gentamycin and resuspended in equal volumes of HBSS and chilled 10% DMSO+4% human serum albumin. Aliquots containing 1.5-2×10^7 viable tumor cells stored under liquid Nitrogen.

Robert O et al. described Irradiated Cells from Autologous Tumor Cell Lines as Patient-Specific Vaccine Therapy in 125 Patients with Metastatic Cancer: Induction of Delayed-Type Hypersensitivity to Autologous Tumor is Associated with Improved Survival in Cancer biotherapy and Radiopharmaceuticals Volume 17, Number 1, 2002. They established short-term cultures of pure tumor cells for use as autologous tumor cell vaccines in an effort to study the effects of patient-specific immunotherapy. Surgically resected fresh tumor was obtained from patients with metastatic cancer. Successful tumor cell lines ($5 \times 10^7$) were expanded to $10^8$ cells, irradiated, and cryopreserved for clinical use. Following a baseline test of delayed-type hypersensitivity (DTH) to an i.d. injection of $10^6$ irradiated autologous tumor cells, patients received 3 weekly s.c. injections of $10^7$ cells, had a repeat DTH test at week-4, then received monthly vaccinations for 5 months. A positive DTH test was defined as ≥10 mm induration; survival was determined from the first DTH test.

Dillman R O et al described Establishing in vitro cultures of autologous tumor cells for use in active specific immunotherapy in emphasis Tumor Immunol. 1993 July; 14(1): 65-9F They harvested fresh tumors and attempted to establish short-term cultures of tumor cells to obtain 10(8) cells which could subsequently be used in autologous tumor cell vaccine programs. Fresh tumors were mechanically processed to initiate primary cultures in RPM1-1640 containing 1 mM sodium pyruvate, 2 mM glutamine, 10 mM N-(2-hydroxyethyl) piperazine-N'-(2-ethanesulfonic acid), 15% fetal bovine serum, and antibiotics, incubated at 37 degrees C. in 5% CO2. We were successful in growing 87 of 142 [61%, (95% confidence limits [55-68%]) of all tumors] including 39 of 58 (67%) melanomas, 10 of 10 (100%) renal cell carcinomas, 14 of 14 (100%) sarcomas, and 23 of 54 (43%) various adenocarcinomas.

Jaffee E M described Development and characterization of a cytokine secreting pancreatic adenocarcinoma vaccine from primary tumors for use in clinical trials in *Cancer journal from scientific American*, Vol. 4, issue 3, PP: 194. Freshly digested tumor cells were plated in duplicate at $2*10^6$ cells per 25 cm2 flasks. Each growth condition was evaluated both separately and in combination with other growth supplements. Different media including RPMI, DMEM, Ham's and Aim V preparation, and lots of FBS were the initial components of growth media screened. After identification of the optimal medium and serum, additional additives were systematically evaluated. Each supplement was evaluated until either epithelial or fibroblastic like cells predominated in the cultures.

The book "Culture of animal cells—A manual of Basic technique", Fifth edition, Protocol-24.3, pp: 429-430 also describes the methods of growing primary cells and tumors and establishing them as cell lines.

List of Cancer Cells Available from Various Repositories.

Cervical cancer: HeLa S3, HeLa 229, H1HeLa, Hs 588.T, GH329, GH354, HeLa NR1, C-4 I, C-4 II, DoTc2 4510, C-33 A, SW756 SiHa Colon cancer: NCI-H548, Hs 255.T, HCT-8 (HRT-18), Hs 675.T Bladder cancer: Hs 195.T, Hs 228.T, Hs 172.T5637, HT-1376 HT-1197, UM-UC-3, SW 780, J82 SCaBER, T24, TCCSUP, Hs 789.T, Hs 769.T, RT4

Renal Cancer: A704, A-704, NCI-H1373, NCI-H1395, Hs 618.T, SK-LU-1, HCC2935, HCC4006, HCC827, ACHN 786-O769-P, Caki-2 HTB-47, A-498 A549, A-427, SW 156, G-402, Hs 926.1, G-401

Breast Cancer: Hs 274.T, Hs 280.T, Hs 281.T, Hs 343.T, Hs 362.T, Hs 739.T, Hs 741.T, Hs 742.T, Hs 190.T Hs 319.T Hs 329.T Hs 344.T Hs 350.T Hs 371.T Hs 748.T Hs 841.T Hs 849.T Hs 851.T Hs 861.T Hs 905.T Hs 479.T, Hs 540.T, Hs 566(B).T, Hs 605.T, Hs 606 BT-20, HT 762.T, UACC-812, HCC1954 Hs 574.T BT-483 BT-549, DU4475, Hs 578T, BT-474, HCC1806, UACC-893, HCC38, HCC70, HCC202, HCC1143, HCC1187, HCC1395, HCC1419, HCC1500, HCC1599, HCC1937, HCC2157, HCC2218, HCC1569

Ovarian Cancer: Caov-3, TOV-21G, Hs 38.T, Hs 571.T, ES-2, TE 84.T

Pancreatic Cancer: BxPC-3, HPAF-II, HPAC, Panc 03.27, Panc 08.13, Panc 02.03, Panc 02.13, Panc 04.03, Panc 05.04, Cagan-2, CFPAC-1, PL45, Panc 10.05, MIA PaCa-2, PANC-1

Lung Cancer: Hs 229.T, NCI-H2135, NCI-H2172, NCI-H2444, NCI-H835, UMC-11, NCI-H727, NCI-H720, Hs 573.T, NCI-H596 NCI-H1688, NCI-H1417, NCI-H1836, NCI-H1672 HLF-a, NCI-H292, NCI-H2126, Calu-6, NCI-H2170, NCI-H520, SW 900, Hs 57.T Colorectal cancer: NCI-H716, NCI-H747, NCI-H508, NCI-H498, SNU-C2B, SNU-C2A, LS513, LS1034, LS411N, WiDr, COLO 320DM, COLO 320HSR, DLD-1, HCT-15, SW480, SW403, SW48, SW1116, SW948, SW1417, LS123, LS 180, LS 174T, C2BBe1, Hs 257.T, Hs 587.Int, Caco-2, HT-29, HCT 116, ATRFLOX, SW1463, Hs 200.T, Hs 219.T, Hs 722.T.

Non-small cell lung cancer: NCI-H1581 NCI-H23, NCI-H522, NCI-H1435, NCI-H1563, NCI-H1651, NCI-H1734, NCI-H1793, NCI-H1838, NCI-H1975, NCI-H2073, NCI-H2085, NCI-H2228, NCI-H2342, NCI-H2347, NCI-H2066, NCI-H2286, NCI-H1703, SW 1573, NCI-H358, NCI-H810, DMS 79, DMS 53, DMS 114, SW 1271, NCI-H2227, NCI-H1963, SHP-77, H69AR Skin Cancer: 182-PF, SK 166-ME, SK, TE 354.T, A-431, A431NS, A253*, Hs 357.T, Hs 941.T, Hs 295.T, Hs 63.T, Hs 892.T, Hs 898.T, Hs 416.T, Hs 925.T, Hs 156.T, WM-115, Hs 600.T, Hs 688(A).T, Hs 839.T, Hs 852.T, Hs 906(A).T, Hs 906(B).T, Hs 908.Sk, Hs 936.T, Hs 936.T (C1), Hs 939.T, A101D CHL-1, HMCB (Human Melanoma Cell Bowles), C32TG, C32, G-361, A-375, A375.S2, COLO 829, Hs 940.T, HT-144, Malme-3M, RPMI-7951, SK-MEL-5, SK-MEL-24, SK-MEL-28 SK-MEL-31, WM278,451Lu, WM1552C, WM35, WM793B, 1205Lu, WM39, A7

Liver Cancer: C3A, SNU-398, SNU-449, SNU-182, SNU-475, Hep 3B2.1-7, Hep G2, SNU-387, SNU-423, PLC/PRF/5

Brain cancer: A172, U-138 MG, DBTRG-05MG, LN-18, LN-229, U-87 MG, U-118 MG, M059K, M059J, LNZTA3WT4, LNZTA3WT11, Hs 683, PFSK-1, CHP-212, IMR-32, H4 Bone/Bone Marrow cancer: Hs 819.T, SW 1353, TF-1, TF-1a, TF-1.CN5a.1, HEL 92.1.7, KG 1, Hs 709.T, Hs 454.T, NCI-H929, 143.98.2, G-292, done A141B1, MG-63, HOS, KHOS/NP (R-970-5), KHOS-240S, KHOS-321H, MNNG/HOS (CI #5), Hs 3.T, Hs 39.T, Hs 184.T, Hs 188.T, Hs 387.T, Hs 704.T, Hs 707(A).T, Hs 735.T, Hs 755(B).T, Hs 781.T, Hs 792(B).T, Hs 805.T, Hs 811.T, Hs 866.T Hs 870.T, Hs 871.T, Hs 889.T, Hs 890.T, R-970-5, TE 417.T, TE 418.T, TO 203.T, HT 728.T, Hs 14.T, T1-73, 143B, 143B PML BK TK, Saos-2, U-2 OS, Hs 88.T, Hs 864.T, SJSA-1, Hs 900.T, Hs 903.T, Hs 919.T, SK-ES-1, Hs 706.T, Hs 737.T, Hs 821.T, Hs 846.T, Hs 883.T Hs 822.T, Hs 863.T, RD-ES, TE 76.T, TE 130.T, Hs 814.T, Hs 324.T, SW 982, MEG-01

Blood cancer: SUP-B15, CCRF-SB, 8E5, TALL-104, MOLT-4, CCRF-CEM, CCRF-HSB-2, MOLT-3, CEM/C2, CEM/C1, THP-1 TIB-202, AML-193, Kasumi-1 Kasumi-3, BDCM, AML14.3D10/CCCKR3 Clone 16, Kasumi-6, HL-60, Clone 15 HL-60, HL-60/MX2, HL-60/MX1, J.CaM1.6, Jurkat, Clone E6-1, J.RT3-T3.5, D1.1, J45.01, MV-4-11, Kasumi-4, KU812, KU812E, KU812F, RPMI 6666, U266B1, RPMI 8226, Mo, Mo-B, SUP-T1, JM1, GDM-1, CESS, ARH-77,1A2, H9/HTLV-IIIB, HuT 78, JSC-1, BCP-1,2B8, Daudi, EB-3, Raji, Jiyoye, NAMALWA, HS-Sultan, CA46, GA-10, GA-10 (Clone 4), GA-10 (Clone 20), NC-37,20B8, HKB-11,1G2, HH, H9, MJ, BC-1, BC-2, Toledo, U-937, TUR, DB, BC-3

Sarcoma: TE 441.T, TE 617.T, Hs 729.T, TE 381.T, RD, A-673, Hs 729, A-204, Hs 94.T, Hs 132.T, Hs 127.T, Hs 701.T, HT-1080, Hs 778(A).T, Hs 778(B).T, Hs 15.T SW 684, TE 115.T, Hs 93.T, Hs 934.T, Hs 935.T Lymph node Cancer: Hs 604.T, Hs 751.T, Hs 445, Hs 611.T, Hs 616, Hs 505.T, Hs 491.T

SUMMARY OF INVENTION

The object of present invention is to alter immunogenic profile of cancer cells in such a way that they become better immunogen.

The object of present invention is to alter immunogenic profile of cancer cells in such a way that they are immunogenic against heterogeneous cancer antigen/s specific to tissue/organ The object of present invention is to provide therapeutic vaccine for use in treatment of malignant tumor/s having immunogenicity against heterogeneous cancer antigen/s specific to tissue/organ.

It is yet another object of invention is to provide method of preparing the therapeutic vaccine for use in treatment of malignant tumor/s having immunogenicity against heterogeneous cancer antigen/s specific to tissue/organ.

It is another object of invention is to provide an antigen for therapeutic vaccine for use in treatment of malignant tumor/s which elicits immune response against heterogeneous cancer cells specific to tissue/organ.

It is another object of invention to provide allogeneic cancer vaccine without inducing carcinogenicity.

It is yet another objective to provide therapeutic vaccines for malignant tumor/s that stimulate the cell mediated immune response specific to homologous as well as hetrologous cancer cells specific to tissue/organ.

It is yet another objective to provide therapeutic vaccines for malignant tumor/s that stimulate humoral immune response specific to homologous as well as hetrologous cancer cells specific to tissue/organ.

DETAILED DESCRIPTION

Figure 1:
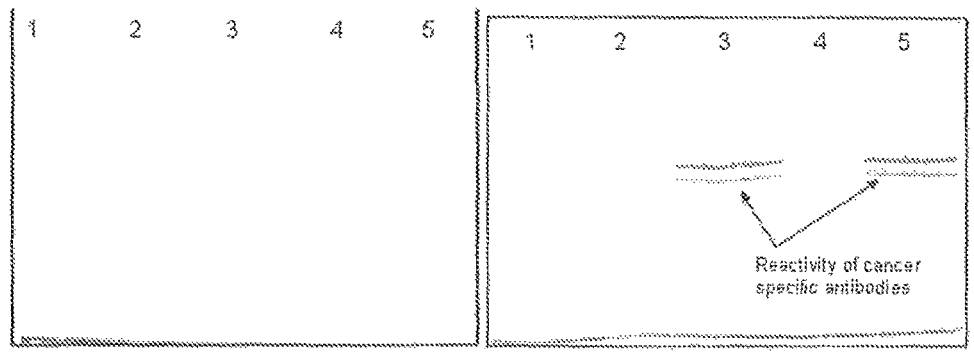
FIG. 1: Immune reactivity of cancer vaccine preparation to homologous cancer cells of pancreatic origin as determined by antibody detection using western blot as per present invention.

Surprisingly it is observed that cancer cells change their immunological characteristics in presence of *Mycobacterium* w. After change in immunological characteristics, Cancer cells possess immunogen, which are shared by heterogeneous cancer cells specific to tissue/organ. However immunogen so acquired do not react to normal cells as well as tumor arising from other organ/tissue.

Thus according to present invention the immunogenic profile of cancer cells originating from an organ in presence of *Mycobacterium* w (Mw) gets altered. Due to the altered immunogenic profile the cancer cells generates immune response against homogenous cells as well as heterogeneous cells present in/arising form same organ/tissue. The generation of immune response against heterogeneous cell is typically not seen with cancer cells.

The cancer cells as per present invention changes immunogenic profile when the intracellular p38 levels. The cancer cells of present invention can be live, killed, or in the state of senescence The cancer cells of the present invention can be killed by but not restricted to physical treatment, and/or chemical treatment.

The cancer cells of the present invention killed by heating or boiling or treated with steam.

The cancer cells of the present invention killed by treatment with chemicals/substances such as aldehyde, keton, acid, alkali, salt, ether, ester etc.

The ratio of cancer cells to *Mycobacterium* w for the present invention is in range from 10:1 to 1:10000 which results in change in immunological characteristics of cancer cells.

The ratio of cancer cells to *Mycobacterium* w for the present invention is preferably in range of 1:10 to 1:1000.

The most preferred ratio of cancer cells to *Mycobacterium* w for the present invention is in range of 1:10 to 1:100.

As per the present invention it is not necessary that cancer cells to be inside the body to acquire this novel immunogenic profile.

The time for which the presence of *Mycobacterium* w is required to alter immunogenic profile of cancer cells is one minute or more. It can be till administration of cancer cells into the body.

The temperature at which the change in immune profile cancer cells takes place ranges from 1° to 60° C.

The media environment required for change in immune profile of cancer cells is selected from saline, buffer, nutrition media or combination thereof. The nutrition media is a media in which cancer cells are propagated and/or kept alive.

As per present invention cancer cells die in presence of *Mycobacterium* w.

As per present invention the death induced by *Mycobacterium* W is more than 10% of total cells, preferably more than 30% and most preferably 60 to 80% of total cancer cells.

The cancer cell/s for the purpose of the invention can be live cancer cell/s or killed cancer cell/s.

As per present invention cancer cells having achieved the immunological profile, retain the same even when they are killed. The cancer cells prepared as per present invention induce immune response.

The cancer cell used in the invention can be allogeneic cancer cell/s or autologous cancer cells. The allogeneic cancer cells are isolated, purified, derived and/or modified from the other organism/mammal/human/patient of same species. The allogeneic cancer cells can also be established and/or immortalized cell line produced or purchased from repositories.

The autologous cancer cells are isolated, purified, derived and/or modified from the same organism/mammal/human/patient.

*Mycobacterium* w is a non-pathogenic strain of *Mycobacterium* spps that was isolated from soil. Genome wide comparisons together with molecular phylogenetic analyses by fluorescent amplified fragment length polymorphism (FAFLP), enterobacterial repetitive intergenic consensus (ERIC) based genotyping and candidate orthologues sequencing revealed that Mw has been the predecessor of highly pathogenic *Mycobacterium avium*-intracellulare complex (MAIC) that did not resort to parasitic adaptation by reductional gene evolution and therefore, preferred a free living life-style. Further analysis suggested a shared aquatic phase of MAIC bacilli with the early pathogenic forms of *Mycobacterium*, well before the latter diverged as 'specialists' (Ahmed N, et al (2007) Molecular Analysis of a Leprosy Immunotherapeutic *Bacillus* Provides Insights into Mycobacterium Evolution. PLoS ONE 2(10): e968) The organism gives negative results when tested with urease, tween 80 hydrolysis and niacin. It gives positive result with nitrate reduction test.

The altered immunologic profile of cells manifests into altered immune response by the immune system of the host administered with the vaccine. The altered immune response can be determined by determining cell mediated immune response or/and humoral response. The common methods deployed for the purpose are ELISPOT, Effector function, Western blot etc.

The efficacy of therapeutic cancer vaccine is determined by its ability of inducing immune response against the specific antigen and also its ability to react to the antigen. For the current invention the antigens are the cancer cells with altered immunological properties by co-incubating cancer cells with *Mycobacterium* W.

The efficacy of these cancer cells was determined for both ability to induce and react to the antigen by immune system of suitable host. The efficacy of the therapeutic vaccine to induce immune response was studied by determining increase in number of cells producing interferon gamma in response to antigen by ELISPOT. The technique provided indication of inducing cell mediated immune response. The humoral immune response was studied using sera of mice to detect presence of specific antibody response to the vaccine.

Similarly the ability to induce heterogeneous immune response but specific to tissue/organ was also determined by specific immune response in response to stimulus of non-homologous tissue/organ specific cancer cell lines (heterogeneous). The heterogeneous response was also evaluated for both cell mediated using interferon gamma ELISPOT and humoral response using western blot.

The ability to react to the target cells was determined using effector function. The effector function is the method by which it is determined that whether the target cell (cancer) is killed by the cells of immune system stimulated/activated by administration of vaccine. The therapeutic cancer vaccine showed killing of target cancer cells of both types i.e. homologous and heterogeneous cancer cells of same tissue/organ.

Example 1: Process of Altering the Immunogenic Profile of Cancer Cells in such a Way that they are Immunogenic Against Heterogeneous Cancer Antigen/s Specific to Tissue/Organ A) Allogeneic Mia-paca-2 cancer cells are harvested and washed with Dulbecco's Phosphate buffer saline (DPBS) to remove traces of serum. Viable cells are counted and "*Mycobacterium* W" is added to the cells at a cell: "*Mycobacterium* W" ratio of 1:100. This cell suspension is incubated at 37° C. for 6 hrs. The cell suspension is centrifuged at 350 g for 10 minutes to separate and remove "*Mycobacterium* W". The intracellular p38 levels are measured. The cells with increased p38 levels are used as a vaccine or may be further formulated. The adjutant/s may be added to it if desired.

B) Allogeneic B16 melanoma cancer cells are harvested and washed with DPBS to remove traces of serum. Viable cells are counted and "*Mycobacterium* W" is added to the cells at a cell: "*Mycobacterium* W" ratio of 1:100. This cell suspension is incubated at temperature 10° C. till it is administered preferably for 4-6 hrs. The intracellular p38 levels are measured. The cells with increased p38 levels are used as a vaccine or may be further formulated. The adjutant/s may be added to it if desired.

C) Allogeneic cancer cells NFS60 (leukemic cells) are harvested and washed with Dulbecco's Phosphate buffer saline (DPBS) to remove traces of serum. Viable cells are counted and "*Mycobacterium* W" is added to the cells at a cell: "*Mycobacterium* W" ratio of 1:10. This cell suspension is incubated at temperature at 60° C. for 10 minutes. The cells are centrifuged at 350 g for 10 minutes to separate "*Mycobacterium* W". The intracellular p38 levels are measured. The cells with increased p38 levels are used as a vaccine or may be further formulated. The adjutant/s may be added to it if desired.

D) Allogeneic cancer cells (Panc-1) are harvested and washed with DPBS to remove traces of serum. Viable cells are counted and "*Mycobacterium* W" is added to the cells at a cell: "*Mycobacterium* W" ratio of 1:10. This cell suspension is incubated at temperature at 37° C. for 4-6 hrs. The intracellular p38 levels are measured. The cells with increased p38 levels are used as a vaccine or may be further formulated. The adjutant/s may be added to it if desired.

E) Allogeneic cancer cells A549 (Lung cancer) are harvested and washed with Dulbecco's Phosphate buffer saline (DPBS) to remove traces of serum. Viable cells are counted and "*Mycobacterium* W" is added to the cells at a cell: "*Mycobacterium* W" ratio of 1:1000. This cell suspension is incubated at temperature 37° C. for 4-6 hrs.

The cells are centrifuged at 350 g for 10 minutes to separate "*Mycobacterium* W". The intracellular p38 levels are measured. The cells with increased p38 levels are used as a vaccine or may be further formulated. The adjutant/s may be added to it if desired.

F) Allogeneic cancer cells PC-3 (prostate cancer) are harvested and washed with DPBS to remove traces of serum. Viable cells are counted and "*Mycobacterium* W" is added to the cells at a cell: "*Mycobacterium* W" ratio of 1:1000. This cell suspension is incubated at temperature 25° C. for 24 hrs. The intracellular p38 levels are measured. The cells with increased p38 levels are used as a vaccine or may be further formulated. The adjutant/s may be added to it if desired.

G) Allogeneic cancer cells AsPC are harvested and washed with Dulbecco's Phosphate buffer saline (DPBS) to remove traces of serum. Viable cells are counted and "*Mycobacterium* W" is added to the cells at a cell: "*Mycobacterium* W" ratio of 1:10000. This cell suspension is incubated at temperature at 30° C. for 6 hrs. The cells are centrifuged at 350 g for 10 minutes to separate "*Mycobacterium* W". The intracellular p38 levels are measured. The cells with increased p38 levels are used as a vaccine or may be further formulated. The adjutant/s may be added to it if desired.

H) Allogeneic cancer cells Mia-paca-2 are harvested and washed with DPBS to remove traces of serum. Viable cells are counted and "*Mycobacterium* W" is added to the cells at a cell: "*Mycobacterium* W" ratio of 1:10000. This cell suspension is incubated at temperature 37° C. for 120 minutes. The intracellular p38 levels are measured. The cells with increased p38 levels are used as a vaccine or may be further formulated. The adjutant/s may be added to it if desired.

I) Allogeneic cancer cells MCF 1 (Breast Cancer) are harvested and washed with Dulbecco's Phosphate buffer saline (DPBS) to remove traces of serum. Viable cells are counted and "*Mycobacterium* W" is added to the cells at a cell: "*Mycobacterium* W" ratio of 1:1. This cell suspension is incubated at temperature 40° C. for 5 hrs. The cells are centrifuged at 350 g for 10 minutes to separate "*Mycobacterium* W". The intracellular p38 levels are measured. The cells with increased p38 levels are used as a vaccine or may be further formulated. The adjutant/s may be added to it if desired.

J) Allogeneic cancer cells isolated from patient suffering from melanoma are cultured in laboratory are harvested and washed with DPBS to remove traces of serum. Viable cells are counted and "*Mycobacterium* W" is added to the cells at a cell: "*Mycobacterium* W" ratio of 1:1. This cell suspension is incubated at temperature 50° C. for 4-6 hrs. The intracellular p38 levels are measured. The cells with increased p38 levels are used as a vaccine or may be further formulated. The adjutant/s may be added to it if desired.

K) Allogeneic cancer cells (Panc-1) are harvested and washed with DPBS to remove traces of serum. Viable cells are counted and "*Mycobacterium* W" is added to the cells at a cell: "*Mycobacterium* W" ratio of 1:10. This cell suspension is incubated at temperature at 37° C. for 4-6 hrs. The Mw added are separated by centrifuged at 350 g for 10 minutes. The intracellular p38 levels are measured. The cells with increased p38 levels are used as a vaccine or may be further formulated. The adjutant/s may be added to it if desired.

L) Allogeneic cancer cells isolated from patient suffering from melanoma are cultured in laboratory are harvested and washed with DPBS to remove traces of serum. Viable cells are counted and "*Mycobacterium* W" is added to the cells at a cell: "*Mycobacterium* W" ratio of 1:1. This cell suspension is incubated at temperature 50° C. for 4-6 hrs. The Mw added are separated by centrifugation at 350 g for 10 minutes. The intracellular p38 levels are measured. The cells with increased p38 levels are used as a vaccine or may be further formulated. The adjutant/s may be added to it if desired.

Example 2: Following Example Illustrates Improved Immune Response as Per Present Invention Without Limiting the Scope of Invention A. Therapeutic Vaccine Elicits Cell Mediated Immune Response Against Homologous Cancer Cells as Demonstrated by Interferon Gamma ELISPOT.

Therapeutic Cancer vaccines prepared by the method described in example 1 are immunogenic and elicit a Th1 type of immune response as demonstrated by immunogenicity studies in mouse model. Briefly, mice were immunized intra-dermally with vehicle control or vaccine formulation containing 2×10^6 cells on day 0 and 21. The animals were euthanized by CO2 over exposure on day 28 and immune status was determined as studied by the number of IFN-g secreting cells amongst splenocytes. A significant increase (8.4 fold) was found in the number of IFN-g secreting cells in the Group immunized with vaccine formulation compared to Vehicle Control as depicted in Table: 1

TABLE 1

| Immunogenicity of Cancer Vaccine determined by the number of IFN-g secreting-cells | |
|---|---|
| Group | Interferon gamma producing cells per 0.1 million splenocytes |
| Vehicle control | 15 cells |
| Cancer vaccine | 126 cells |

B. Therapeutic Vaccine Elicits Immoral Immune Response Against Homologous Cancer Cells as Demonstrated by Antibody Reactivity to Lysates of Homologous Cancer Cells by Western Blot.

Mice were randomized in two groups. First group of mice were immunized intradermally at 0 and 21 day with therapeutic cancer vaccine prepared as per example 1-6 while second group i.e. control group were immunized with PBS. Serum samples from all of the mice were isolated at 28th day of study to detect the generation of antibody against vaccine.

Western blot of homologous cancer cell (Miapaca-2) lysate was performed with sera samples of mouse from either group. The detection of antibody bound with lysate protein, HRP conjugated goat Anti-mouse IgG antibody was used with DAB (Diamino Benzidine) as coloring agent and $H_2O_2$ as substrate.

From western blot analysis as shown in FIG. 1 it is found that therapeutic cancer vaccine immunization generates antibody response against Homologous cell lysate.

Figure 2:
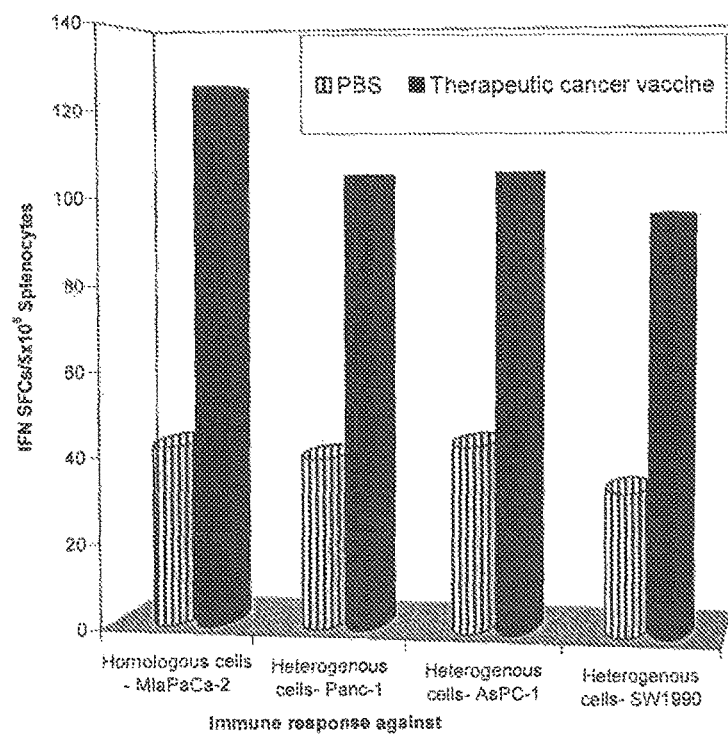
FIG. 2: Immune reactivity of cancer vaccine preparation as per present invention to homologous as well as heterogeneous cancer cells of pancreatic origin determined by the number of IFN-g secreting cells

Example 3: Following Example Illustrates Immune Response Against Heterogeneous Cancer Cells Specific to Tissue/Organ as Per Present Invention Without Limiting the Scope of Invention A. Therapeutic Vaccine Elicits Call Mediated Immune Response Against Heterogeneous Cancer Cells Specific to Tissue/Organ as Demonstrated by ELISPOT-Rise in Interferon Gamma Producing Cells Mice were immunized intra-dermally with control or $2\times10^6$ Mia-para-2 cells for cancer vaccine formulation prepared as in example 1 on day 0 and 21. On day 28 mice were euthanized by over-exposure of CO2. The spleen from each mouse was collected and splenocytes isolated. $5\times10^5$ splenocytes from each mice were seeded in ELISPOT plates from R & D Systems coated with capture antibody for IFN-g. The cells were stimulated in-vitro with 10 ug/ml of lysates of Mia-PaCa-2, Panc-1 and AsPC-1 and incubated at 37° C. and 6% CO2 for ~36 hrs. At the end of the incubation period the plates were developed as per the manufactures instructions. Briefly, the cells were washed off and detection antibody was added. The plate was incubated for 2 hrs at room temperature. Streptavidin-ALP conjugated enzyme was then added followed by addition of precipitating substrate BCIP-NBT. The spots were counted using an automated immunospot reader. Immune reactivity of cancer vaccine preparation to homologous (Mia-para-2 cells) as well as heterogeneous cancer cells (Panc-1 and AsPC-1) of pancreatic origin was determined by the number of IFN-g secreting cells as depicted in the FIG. 2. The finding suggest that cancer vaccine prepared as per present invention using mia-paca-2 cells is able to generate immune response not only against Mia-paca-2 cells (homologous) but also against Panc-1 and AsPC-1 cells (heterogeneous). There is no significant difference in immune response generated against various cell types.

Figure 3:
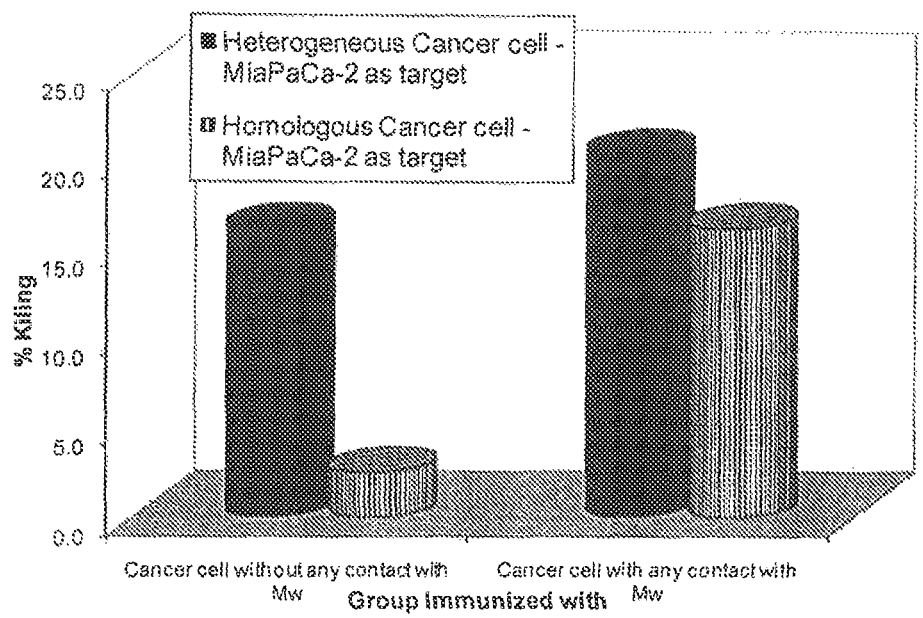
FIG. 3: Immune reactivity of cancer vaccine preparation as per present invention to homologous as well as heterogeneous cancer cells of pancreatic origin as determined by killing of homologous as well as heterogeneous cancer cell.

B. Therapeutic Vaccine Elicits Cell Mediated Immune Response Against Heterogeneous Cancer Cells Specific to Tissue/Organ as Demonstrated by Effector Function—Killing of Target Cancer Cells Balb/c mice were immunized with either cancer cells (Mia-Paca-2) or therapeutic cancer vaccine prepared as per example 1-6 on day 0 and 21. The mice were sacrificed and Splenocytes isolated were used as effector cells against Mia-paca2 and Panc-1 cell line. The results depicted in FIG. 3 shows therapeutic cancer vaccine is able to produce cross immunization in cancer cells. The therapeutic cancer vaccine shows effector function against both the cell lines that is to homologous (Mia-pica-2 cells) as well as heterogeneous cancer cells (Pant-1 and AsPC-1) of pancreatic origin.

C. "*Mycobacterium* W" Treatment Increases the Cross Presentation of Cancer Cells to Provide Heterogeneous Immunity First group of mice were immunized intradermally on 0 and 21 day with MiaPaCa-2 cells while second group with therapeutic cancer vaccine as prepared in example 1-6. The splenocyte suspension ($10^7$ cells/mL) from all of the mice was prepared at day 28 of study to estimate IFN-g secreting cells by ELISPOT.

Figure 4:
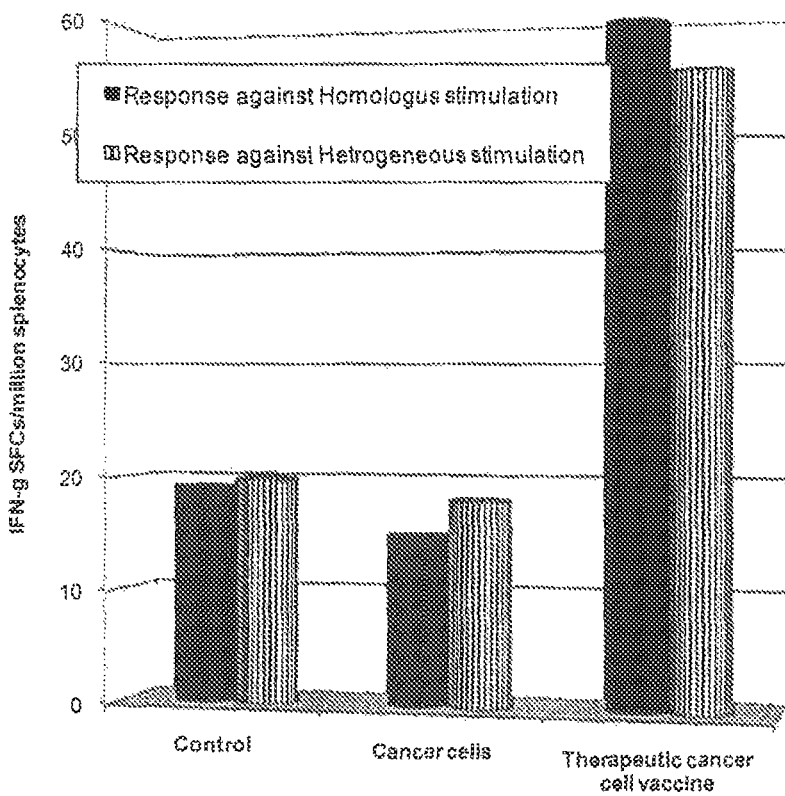
FIG. 4: Immune reactivity of cancer vaccine preparation as per present invention to homologous as well as heterogeneous cancer cells of pancreatic origin as determined by killing of homologous as well as heterogeneous cancer cell.

The splenocyte cells of both control and test groups were added to ELISPOT plate in different wells at a density of $1\times10^6$ cells/well. The plates were incubated at 37° C. and 6% CO2 for 36-48 hrs. After the incubation period was completed, the cells were decanted off from the plate and washed with DPBS. 100 ul of 1:100 diluted detection antibodies was added to each well. The plate was incubated at 4° C. overnight following which it was washed and tapped dry. Streptavidin-ALP conjugate was diluted 1:1000 in PBS-0.5% FBS. 100 µl of 1:1000 diluted streptavidin-ALP conjugate was added in each well followed by incubation at room temperature for 1 hour in dark. The plate was washed and tapped dry. 100 µl of the BCIP-NBT substrate was added to each well. Again the plate was incubated at room temperature in dark until distinct spots emerged. The reaction was stopped by washing the plate with water. The plate was the kept for drying overnight at 37° C. From the result as shown in FIG. 4 it was apparent that therapeutic cancer vaccine prepared by current invention increases the immune reactivity of mice to hetrogenous cancer cell.

D. Therapeutic Vaccine Elicits Humoral Immune Response Against Hetrologous Cancer Cells of Same Tissue/Organ as Demonstrated by Antibody Reactivity to Lysates of Hetrologous Cancer Cells by Western Blot.

Mice were immunized intradermally at 0 and 21 day with therapeutic cancer vaccine. Serum samples from mice were isolated at 28 day of study to detect the generation of antibody against vaccine and the Heterogeneous reactivity of the mouse cancer vaccine antibody with other cells (heterogeneous) pancreatic origin viz. SW1990 and AsPC, Western blot with lysates of MiaPaCa-2, AsPC-1, SW-1990 and cancers of different origin like HEK-293 (Kidney), PC-3 (Prostate), MCF-7 (Breast), A549 (Lung), PA-1 (Ovary) was performed with primary antibody generated in mouse against therapeutic cancer vaccine. For the detection of primary antibody bound with lysate antigen/s, HRP conjugated goat Anti-mouse IgG antibody was used with DAB (Diamino Benzidine) as coloring/detection agent.

Figure 5:
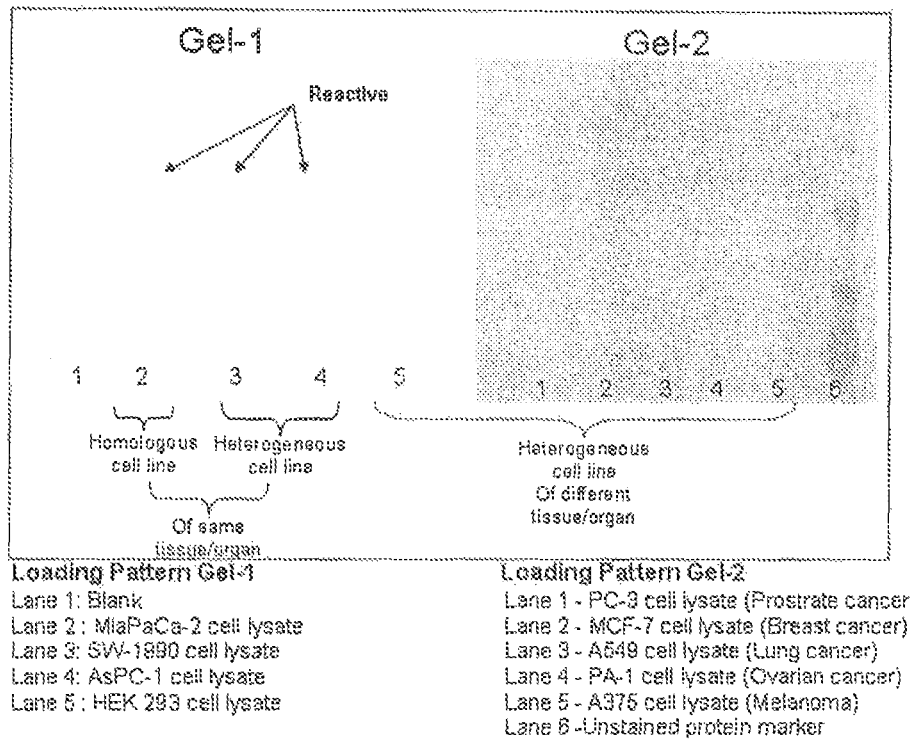
FIG. 5: Immune reactivity of cancer vaccine preparation to homologous as well as heterogeneous cancer cells of pancreatic origin as determined by antibody detection using western blot of homologous as well as heterogeneous cancer cell as per present invention.

Western blot analysis shows (FIG. 5) that Mouse anti-cancer vaccine antibody has heterogeneous reactivity with lysates other cancer cells of pancreatic origin (heterogeneous) while it is non reactive with cancer cell lysates of different tissue/organ.

E. Heat Killed Cancer Cells when Adjuvanted with "*Mycobacterium* W" Generates Immune Response Against Homologous and Herologous Cancer Cells of Same Tissue/Organ as Determined by Effector Function Balb/c mice were immunized with heat killed cancer cells (Mia-paca-2 pancreatic cancer) cells, heat killed cancer cells (Mia-paca-2 pancreatic cancer) cells mixed in ratio 1:100 with "*Mycobacterium* W", administered on day 0 and 21. The mice were sacrificed and Splenocytes isolated on day 28 and were used as effector cells against homologous cancer cell line.

Figure 6:
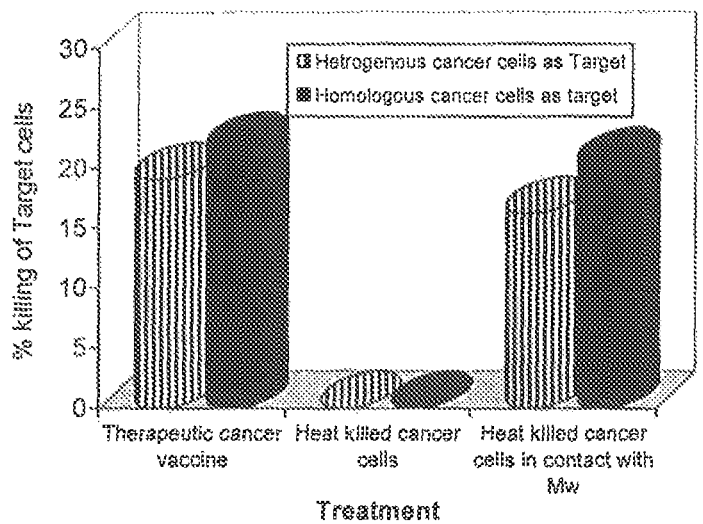
FIG. 6: Addition of "*Mycobacterium* W" improves effector function of heat killed cancer cells as therapeutic cancer vaccine.

The results depicted in FIG. 6 indicate addition of "*Mycobacterium* W" improves efficacy of therapeutic vaccine, using heat killed cells, for use in treatment of malignant tumor/s which elicits immune response against heterogeneous cancer cells specific to tissue/organ as demonstrated by Effector function—Killing of target cancer cells.

F. Formaldehyde Treated Killed Cancer Cells when Adjuvanted with "*Mycobacterium* W" Generates Immune Response Against Homologous and Herologous Cancer Cells of Same Tissue/Organ as Determined by Effector Function Balb/c mice were immunized with formaldehyde treated cancer cells (Mia-paca-2 pancreatic cancer) cells, formaldehyde treated cancer cells (Mia-paca-2 pancreatic cancer) cells mixed in different ratios with "*Mycobacterium* W", on day 0 and 21. The mice were sacrificed and Splenocytes isolated were used as effector cells against homologous cancer cell line.

Figure 7:
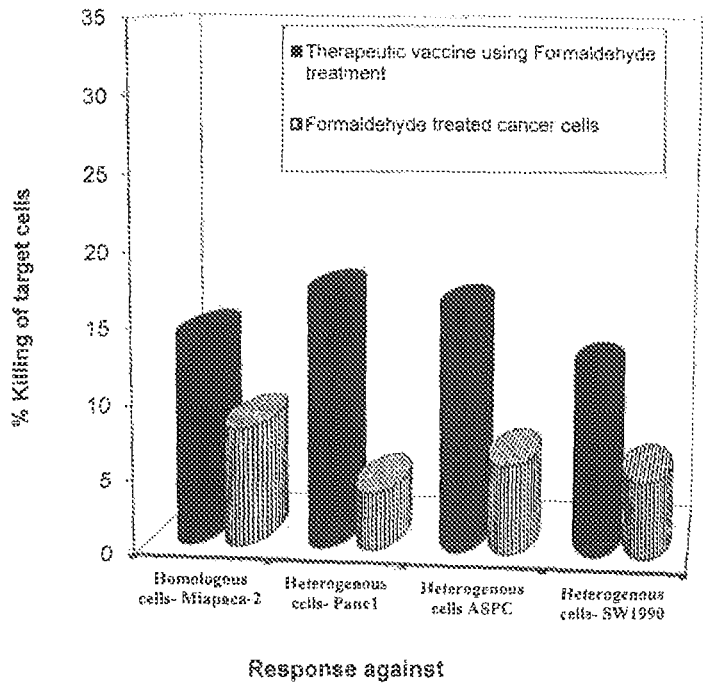
FIG. 7: Addition of "*Mycobacterium* W" improves effector function of formaldehyde treated cancer cells as therapeutic cancer vaccine.

The results depicted in FIG. 7 indicate addition of "*Mycobacterium* W" improves efficacy of therapeutic vaccine, using heat killed cells, for use in treatment of malignant tumor/s which elicits immune response against heterogeneous cancer cells specific to tissue/organ as demonstrated by Effector function—Killing of target cancer cells.

G. Killed Cancer Cells when Adjuvanted with Other Adjuvants Generates Immune Response Against Homologous Cancer Cells of Same Tissue/Organ as Determined by Elispot Assay Balb/c mice were immunized with killed cancer cells (Mia-paca-2 pancreatic cancer) cells mixed with different adjuvants namely "*Mycobacterium* W", BB2, G1, Cadi OFF 10, and combinations thereof; on day 0 and 21. The mice were sacrificed and Splenocytes isolated were used for IFN-gamma ELISPOT homologous cancer cell lysate (FIG. 8).

Figure 8:
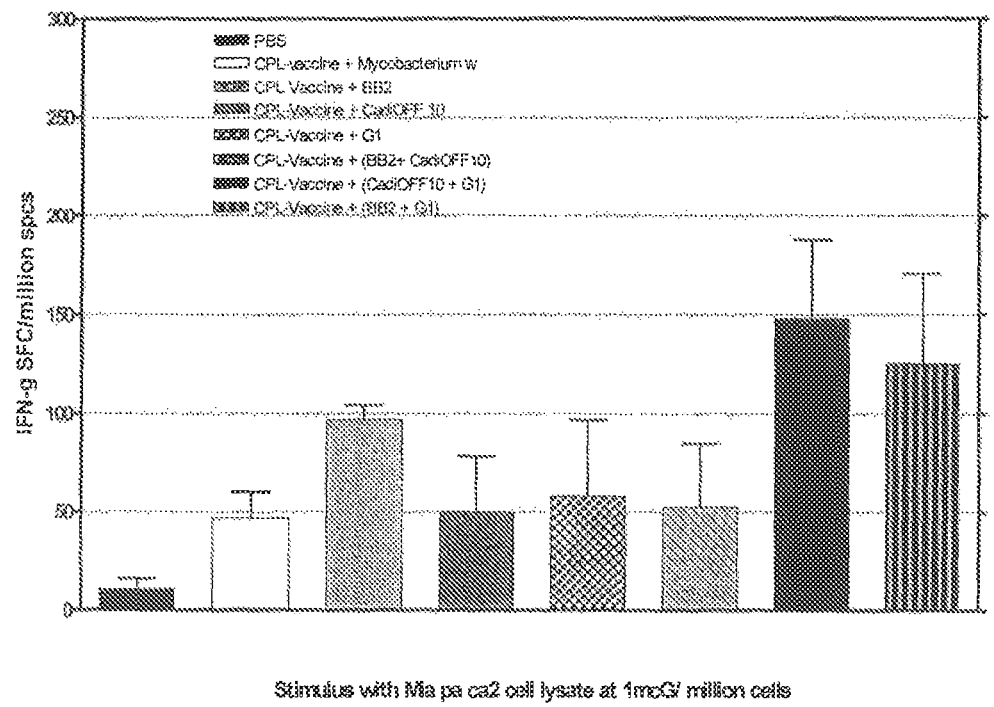
FIG. 8: Addition of different adjuvant(s) improves efficacy of therapeutic cancer vaccine, using killed cancer cells, for use in treatment of malignant tumor(s)

The results depicted in FIG. 8 indicate addition of adjuvant improves efficacy of therapeutic cancer vaccine, using killed cancer cells, for use in treatment of malignant tumor/s.

Example 4: Following Examples Illustrates Treatment of Cancer in Mammals as Per Present Invention Without Limiting the Scope of Invention A. In Vivo Tumor Regression: Treatment of Cancer in a Mammal as Per Present Invention Without Limiting the Scope of Invention Male Balb/C mice (6-8 week), 30 in numbers were used for the study. The animals were randomized on the basis of body weight. The tumor induction was done by injecting $1\times10^5$ B16-F1 cells in hind limb of the mice subcutaneously. Mice were allowed to develop average tumor size of ~100-150 mm3 and randomized in 2 groups 15 mice each on basis of tumor size. First group of mice were immunized intradermally with melanoma vaccine (Prepared as per example 1) on 0 and 10 day post randomization while second group i.e. control mice were kept un-immunized (no treatment). Tumor size was recorded twice a week till the tumor size reached the 10% of animal body weight.

Figure 9:
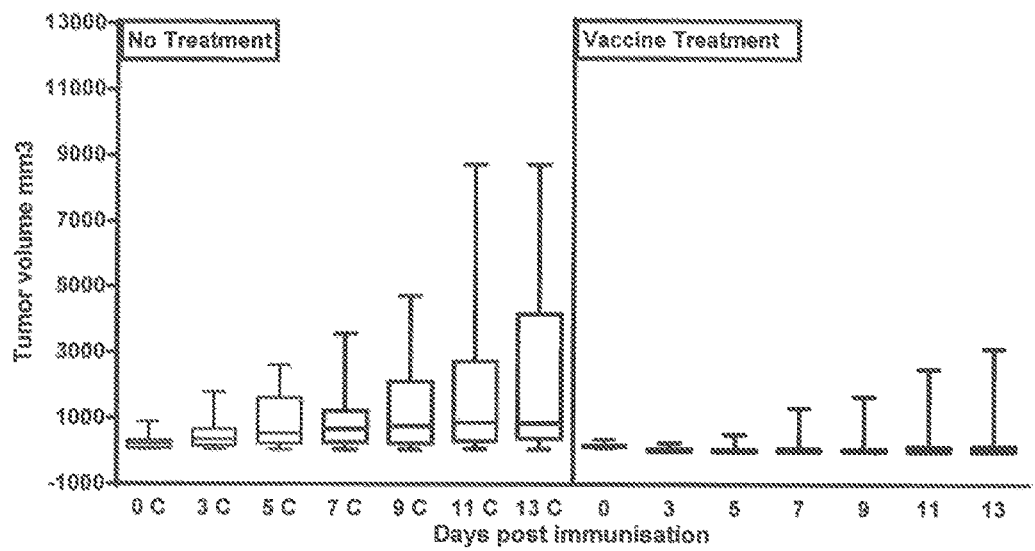
FIG. 9: In vivo Melanoma Tumor regression: treatment of cancer in a mammal as per present invention without limiting the scope of invention

The tumor volume in treatment group did not rise as compared to the untreated group (FIG. 9). The Treatment group in fact showed tumor size reduction indicating the resolution of disease condition. Over all the survival was Improved and tumor size in mice reduced in treatment group.

The treatment group showed delayed progression as well as regression of tumor mass compared to animals with No treatment.

B. In Vivo Tumor Regression: Treatment of Cancer in a Mammal as Per Present Invention without Limiting the Scope of Invention Male C57 mice (6-8 week), 20 in numbers were used for the study. The animals were randomized on the basis of body weight. The tumor induction was done by injecting $1\times10^5$ Pan 02 cells in hind limb of the mice subcutaneously. Mice were allowed to develop average tumor size of ~200 mm3 and randomized in 2 groups 10 mice each on basis of tumor size. First group of mice were immunized intradermally with pancreatic cancer vaccine (Prepared as per example 1) on 0 and 10 day post randomization while second group i.e. control mice were kept un-immunized (no treatment). Tumor size was recorded twice a week till the tumor size reached the 10% of animal body weight.

Figure 10:
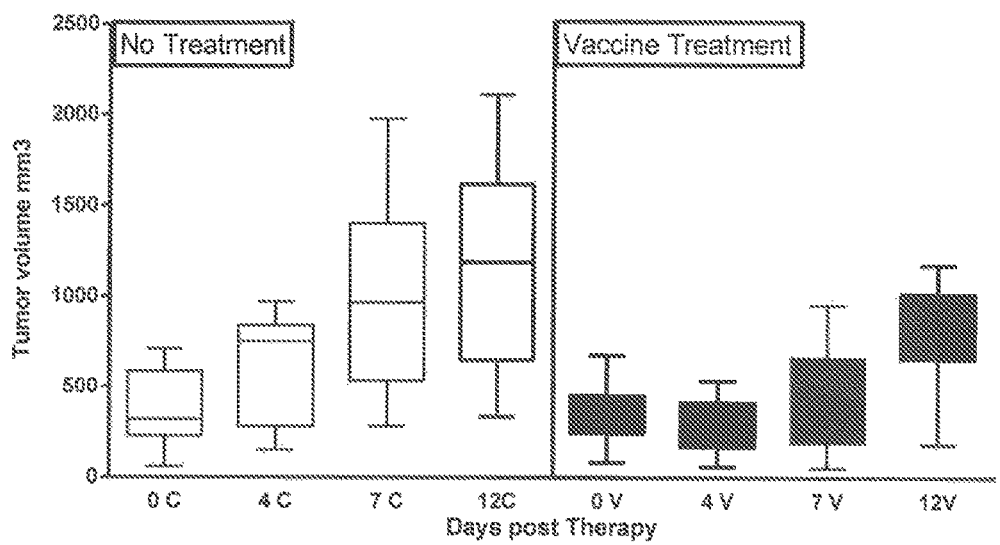
FIG. 10: In vivo pancreatic tumor regression: treatment of cancer in a mammal as per present invention without limiting the scope of invention

The tumor volume in treatment group did not rise as compared to the untreated group (FIG. 10). The Treatment group in fact showed tumor size reduction indicating the resolution of disease condition. Over all the survival was Improved and tumor size in mice reduced in treatment group.

The treatment group showed delayed progression as well as regression of tumor mass compared to animals with No treatment.

These examples clearly demonstrate that the cancer cell vaccine using "*Mycobacterium* W" in preparation enhances its immunogenicity and reactivity against heterogeneous cancer antigen/s specific to tissue/organ.

The other experiments with mice and ex vivo immuno analysis shows that the Cancer cell vaccine is able generate an effector function—meaning the immune system and part there off are able to kill the target cancer cells of heterogeneous nature specific to tissue/organ effectively. The vaccine also shows the efficacy in vivo in treatment of cancer(s).

Thus cancer vaccine used for the management of cancer, in terms of retarding, elevating, or curing cancers. The vaccine can also be used to regresses existing tumors and cancer cell burden.

We claim:

1. A method for inducing an anticancer immune response in a mammalian subject having a cancer, said method comprising harvesting cancer cells cultured in vitro, washing the cells to remove traces of serum, culturing the cancer cells in vitro in the presence of *Mycobacterium* w. for a period of time sufficient to induce the expression by the cancer cells of p38, separating the cancer cells from the *Mycobacterium* w. cells by centrifugation, measuring the level of p38 expression in the cancer cells, collecting cancer cells overexpressing p38 as compared to cancer cells not contacted with *Mycobacterium* w., irradiating or killing the cancer cells, and administering to the subject an effective amount of the irradiated or killed cancer cells overexpressing p38 to induce an anticancer immune response.

2. The method of claim 1 wherein the cancer cells are isolated from a biopsy of a tumor in the subject.

3. The method of claim 1 wherein the cancer cells are isolated from an individual other than the subject and the cancer is of the same type as the cancer in the subject.

4. The method of claim 1 wherein the cancer cells are administered to the subject in combination with an adjuvant.

5. The method of claim 1 wherein the cancer cells are killed by exposing the cells to heat.

6. The method of claim 1 wherein the cancer cells are killed by exposing the cells to a chemical.

7. The method of claim 6 wherein the chemical is formaldehyde.

* * * * *